(12) United States Patent
Meteo de Acosta del Rio et al.

(10) Patent No.: US 6,506,883 B2
(45) Date of Patent: *Jan. 14, 2003

(54) HUMANIZED AND CHIMERIC MONOCLONAL ANTIBODIES THAT RECOGNIZE EPIDERMAL GROWTH FACTOR RECEPTOR (EGF-R); DIAGNOSTIC AND THERAPEUTIC USE

(75) Inventors: Christina Maria Meteo de Acosta del Rio, Ciudad de la Habana (CU); Rolando Pérez Rodríguez, Ciudad de la Habana (CU); Ernesto Moreno Frías, Provincia La Habana (CU)

(73) Assignee: Centro de Inmunologia Molecular, Habana (CU)

( * ) Notice: Subject to any disclaimer, the term of this patent is extended or adjusted under 35 U.S.C. 154(b) by 0 days.

This patent is subject to a terminal disclaimer.

(21) Appl. No.: 09/217,268

(22) Filed: Dec. 21, 1998

(65) Prior Publication Data

US 2002/0065398 A1 May 30, 2002

Related U.S. Application Data

(63) Continuation of application No. 08/560,558, filed on Nov. 17, 1995, now Pat. No. 5,891,996.

(30) Foreign Application Priority Data

Nov. 18, 1994 (CU) ............................................. 128/94

(51) Int. Cl.⁷ .............................................. G07K 16/28
(52) U.S. Cl. .............................. 530/388.22; 530/387.1; 530/388.85; 424/130.1
(58) Field of Search ........................... 530/387.1, 387.3, 530/388.1, 388.22, 388.85; 424/130.1, 133.1, 143.1, 156.1; 435/326, 328, 334

(56) References Cited

U.S. PATENT DOCUMENTS

| | | | |
|---|---|---|---|
| 4,943,533 A | | 7/1990 | Mendesohn |
| 5,470,571 A | | 11/1995 | Herlyn |
| 5,530,101 A | | 6/1996 | Queen |
| 5,558,864 A | * | 9/1996 | Bendig et al. |
| 5,891,996 A | * | 4/1999 | Mataeo De Acosa Del Rio et al. |

FOREIGN PATENT DOCUMENTS

| | | |
|---|---|---|
| EP | 0 586 002 A2 | 3/1994 |
| WO | WO 91/09967 * | 7/1991 |
| WO | WO 92/15683 | 9/1992 |

OTHER PUBLICATIONS

Paul, Fundamental Immunology, Ravin Press NY, chapter 8, p. 242, 1993.*

Rudikoff et al PNAS 79:1979–1983, 1982.*

Carter et al., "Humanization of an anti–pi85$^{HER\ 2}$ antibody for human cancer therapy", *Proc. Natl. Acad. Sci. USA*, vol. 89, pp. 4285–4289, May 1992.

Fernandez et al., "A New Monoclonal Antibody for Detection of EGF–Receptors in Western Blots and paraffin–Embedded Tissue Sections", *Journal of Cellular Biochemistry*, vol. 49, pp. 157–165, 1992.

Kettleborough et al., "Humanization of a mouse monoclonal antibody by CDR–grafting: the importance of framework residues on loop conformation", *Protein Enginnering*, vol. 4, No. 7, pp. 773–783, 1991.

Kettleborough et al., "Isolation of tumor cell–specific single–chain Fv from immunized mice using phage–antibody librariesand the reconstruction of whole antibodies from these antibody fragments", *Eur. J. Immunol.*, vol. 24, pp. 952–955, 1994.

Naramura et al., "Therapeutic potential of chimeric and murine anti–(epidermal growth factor receptor) antibodies in a metastasis model for human melanoma", *Cancer Immunology Immunotherapy*, vol. 37, pp. 343–349, 1993.

Orlandi et al., "Cloning immunoglobulin varible domains for expression by the polymerase chain reaction", *Proc. Natl. Acad. Sci. USA*, vol. 86, pp. 3833–3837, May 1989.

* cited by examiner

Primary Examiner—Sheela Huff
Assistant Examiner—Larry R. Helms
(74) Attorney, Agent, or Firm—TraskBritt

(57) ABSTRACT

Humanized and chimeric monoclonal antibodies that recognize EGF-R and comprise an artificial sequence at least of the FRs of the heavy chain variable region of a human immunoglobulin. The humanized and monoclonal antibodies may comprise variable regions of non-human origin and constant regions of human origin with amino acid substitutions with the variable regions and/or framework regions. Use of the antibodies for therapeutical and diagnostic purposes is also disclosed.

12 Claims, 8 Drawing Sheets

(1 of 8 Drawing Sheet(s) Filed in Color)

FIG. 1A

D V L M T Q I P L S L P V S L G D Q A S I S C <u>R S S Q N I</u>
<u>V H S N G N T Y L</u> D W Y L Q K P G Q S P N L L I Y <u>K V S N</u>
<u>R F S</u> G V P D R F R G S G S G T D F T L K I S R V E A E D
L G V Y Y C <u>F Q Y S H V P W T</u> F G G G T K L E I K R A (SEQ ID NO: 27)

FIG. 1B

Q V Q L Q Q P G A E L V K P G A S V K L S C K A S G Y T F
T <u>N Y Y I Y</u> W V K Q R P G Q G L E W I G G <u>I N P T S G G S</u>
<u>N F N E K F K T</u> K A T L T V D E S S T T A Y M Q L S S L T
S E D S A V Y Y C T R <u>Q G L W F D S D G R G F D F</u> W G Q G
T T L T V S S (SEQ ID NO: 28)

FIG. 2A

```
murine VkR3   D V L M T Q I P L S L P V S L G D Q A S I S C
human. VkR3   D I Q M T Q S P S S L S A S V G D R V T I T C murine VkR3   R S S Q N I V H S N G N T Y L D W Y L Q K P G
human. VkR3   R S S Q N I V H S N G N T Y L D W Y Q Q T P G murine VkR3   Q S P N L L I Y K V S N R F S G V P D R F R G
human. VkR3   K A P K L L I Y K V S N R F S G V P S R F S G murine VkR3   S G S G T D F T L K I S R V E A E D L G V Y Y
human. VkR3   S G S G T D F T F T I S S L Q P E D I A T Y Y murine VkR3   C F Q Y S H V P W T F G G G T K L E I K R A (SEQ ID NO: 27)
human. VkR3   C F Q Y S H V P W T F G Q G T K L Q I T R E (SEQ ID NO: 35)
```

FIG. 2B

```
murine VHR3   Q V Q L Q Q P G A E L V K P G A S V K L S C K A
human. VHaR3  Q V Q L Q Q S G A E V K K P G S S V K V S C K A murine VHR3   S G Y T F T N Y Y I Y W V K Q R P G Q G L E W I
human. VHaR3  S G Y T F T N Y Y I Y W V R Q A P G Q G L E W I murine VHR3   G G I N P T S G G S N F N E K F K T K A T L T V
human. VHaR3  G G I N P T S G G S N F N E K F K T R V T I T V murine VHR3   D E S S T T A Y M Q L S S L T S E D S A V Y Y C
human. VHaR3  D E S T N T A Y M E L S S L R S E D T A F Y F C murine VHR3   T R Q G L W F D S D G R G F D F W G Q G T T L T
human. VHaR3  A R Q G L W F D S D G R G F D F W G Q G S T V T murine VHR3   V S S (SEQ ID NO: 28)
human. VHaR3  V S S (SEQ ID NO: 34)
```

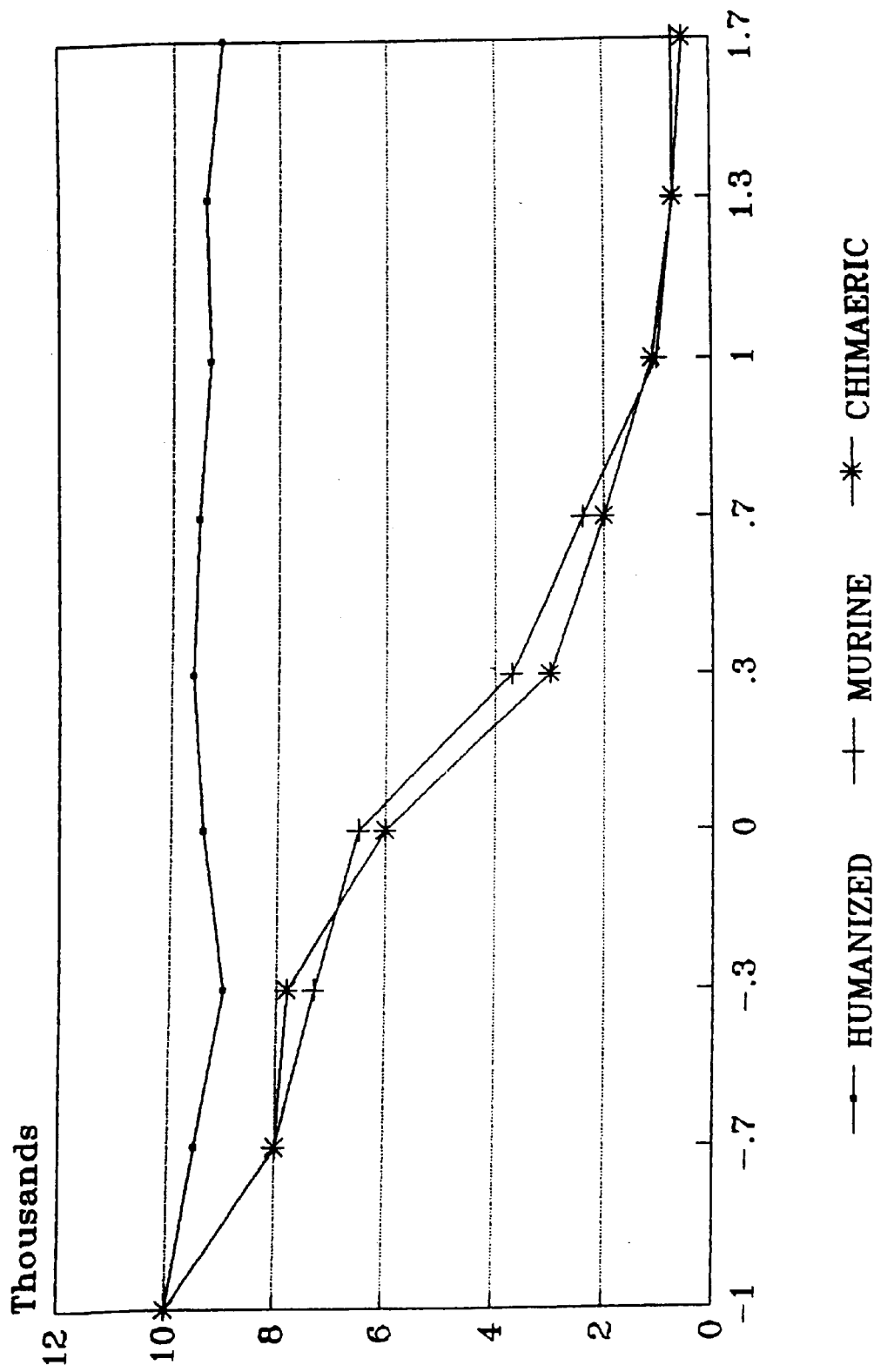

FIG. 5

```
Hum.VH1R3    Q V Q L Q Q S G A E V K K P G S S V K V S C K A
Res.VH2R3    - - - - - - - - - - - - - - - - - - - - - - - -
Res.VH3R3    - - - - - - - - - - - - - - - - - - - - - - - -
Res.VH4R3    - - - - - - - - - - - - - - - - - - - - - - - -
Res.VH5R3    - - - - - - - - - - - - - - - - - - - - - - - -
Res.VH6R3    - - - - - - - - - - - - - - - - - - - - - - - -
Res.VH7R3    - - - - - - - - - - - - - - - - - - - - - - - -

Res.VH1R3    S G Y T F T N Y Y I Y W V R Q A P G Q G L E W I
Res.VH2R3    - - - - - - - - - - - - - - - - - - - - - - - -
Res.VH3R3    - - - - - - - - - - - - - - - - - - - - - - - -
Res.VH4R3    - - - - - - - - - - - - - - - - - - - - - - - -
Res.VH5R3    - - - - - - - - - - - - - - - - - - - - - - - -
Res.VH6R3    - - - - - - - - - - - - - - - - - - - - - - - -
Res.VH7R3    - - - - - - - - - - - - - - - - - - - - - - - -

Res.VH1R3    G G I N P T S G G S N F N E K F K T R V T I T V
Res.VH2R3    - - - - - - - - - - - - - - - - - K A - - - - -
Res.VH3R3    - - - - - - - - - - - - - - - - - - - - - - - -
Res.VH4R3    - - - - - - - - - - - - - - - - - - - - - - - -
Res.VH5R3    - - - - - - - - - - - - - - - - - K A - - - - -
Res.VH6R3    - - - - - - - - - - - - - - - - - - - - - - - -
Res.VH7R3    - - - - - - - - - - - - - - - - - K A - - - - -

Res.VH1R3    D E S T N T A Y M E L S S L R S E D T A F Y F C
Res.VH2R3    - - - - - - - - - - - - - - - - - - - - - - - -
Res.VH3R3    - - - S T - - - - - - - - - - - - - - - - - - -
Res.VH4R3    - - - - - - - - - - - - - - - - - - - - - - - -
Res.VH5R3    - - - - - - - - - - - - - - - - - - - - - - - -
Res.VH6R3    - - - S T - - - - - - - - - - - - - - - - - - -
Res.VH7R3    - - - S T - - - - - - - - - - - - - - - - - - -

Res.VH1R3    A R Q G L W F D S D G R G F D F W G Q G S T V T
Res.VH2R3    - - - - - - - - - - - - - - - - - - - - - - - -
Res.VH3R3    - - - - - - - - - - - - - - - - - - - - - - - -
Res.VH4R3    T - - - - - - - - - - - - - - - - - - - - - - -
Res.VH5R3    T - - - - - - - - - - - - - - - - - - - - - - -
Res.VH6R3    T - - - - - - - - - - - - - - - - - - - - - - -
Res.VH7R3    T - - - - - - - - - - - - - - - - - - - - - - -

Res.VH1R3    V S S
Res.VH2R3    - - -
Res.VH3R3    - - -
Res.VH4R3    - - -
Res.VH5R3    - - -
Res.VH6R3    - - -
Res.VH7R3    - - -
```

An examination of the effects of different reshaped human Vh regions on antigen binding.

ized and Chimeric Monoclonal Antibodies That Recognize Epidermal Growth Factor Receptor (EGF-R); Diagnostic and Therapeutic Use

CROSS-REFERENCE TO RELATED APPLICATIONS

This application is a continuation of application Ser. No. 08/560,568, filed Nov. 17, 1995, now U.S. Pat. No. 5,891,996, issued Apr. 6, 1999, which itself claims priority to Cuban patent application 128/94 filed Nov. 8, 1994, the contents of which are incorporated herein by reference.

TECHNICAL FIELD

The present invention relates to the field of immunology and, in particular, to two new products; chimeric and humanized monoclonal antibodies against epidermal growth factor receptor ("EGF-R"). The chimeric and humanized monoclonal antibodies of the present invention are less immunogenic than original murine monoclonal antibodies and possess improved effector functions.

The present invention also relates to therapeutic and diagnostic compositions comprising these antibodies.

BACKGROUND

The Epidermal Growth Factor ("EGF") is a 53 amino acid polypeptide with a molecular weight of 6045 D and was isolated and purified, for the first time, from murine submaxillary gland. (Cohen S; J Biol Chem (1962) 237, 1555). Later, a similar molecule was obtained from human urine. (Cohen S and Carpenter G; (1975) PNAS USA 72, 1317). The activity of EGF is primarily performed via its interaction with its membrane receptor, a 170 kDa molecular weight glycoprotein. The receptor's intracellular domain is associated with a tyrosine kinase activity and has structural homology to the oncogene v-erb-B showing relation to the malignant transformation process (Heldin C H et al; (1984) Cell 37, 9–20).

High levels of EGF-R have been detected in malignant tumors of epithelium origin such as breast, bladder, ovarian, vulva, colonic, lung, brain and esophagus cancers. The role of EGF and its receptor in regulating tumor growth is unknown, but it has been suggested that EGF-R expression in tumor cells provides a mechanism for autocrine growth stimulation which leads to uncontrolled proliferation (Schlessinger J, Schreiber A B, Levi A, Liberman T and Yarden Y; (1983) Crit Rev Biochem 14(2), 93–111).

It has been reported that EGF produces overgrowth of breast cancer cell lines (Osborne C K et al; (1980) Cancer Research 40, 236 1), as well as modulating the differentiation under some cellular systems (Tonelli C J; Nature (1980) 285, 250–252). These effects on cellular differentiation and proliferation are related to the high expression of EGF-R (Buss J E et al; (1982) PNAS 79, 2574).

The presence of EGF-R in tumor cells has proven to be an indicator of a poor prognosis in human breast cancer. Approximately 40% of the breast tumors show specific binding sites having high affinity for EGF suggesting this growth factor receptor could broaden the concept of hormone dependency in breast cancer (Perez R, Pascual M R, Macias A, Lage A; (1984) Breast Cancer Research and Treatment 4, 189–193). There is also an inverse correlation between the expression of EGF-R and the presence of estrogen receptor, indicating EGF-R as an indifferentiation marker or an indicator of the potential for proliferation of the malignant cells.

Other groups have reported that the expression of EGF-R is higher in regional ganglionar metastasis than in primary carcinomas of breast (Sainsbury J R et al; (1985) Lancet 1, 8425, 364–366) and that the expression of the receptor is different in the different histologic subtypes of human breast carcinoma cells, where presence of the receptor constitutes a signal of a poor prognosis (Macias A et al; Anti Cancer Research 6: 849–852).

The results obtained in different studies have prompted the consideration of the EGF/EGF-R system as a possible target for therapeutic actions.

We obtained a murine monoclonal antibody (R3), raised against the human placenta as described in European Patent application No. 93202428.4, and found to bind to the external domain of the human EGF-R. The R3 antibody was found to inhibit the binding of EGF at both low and high affinity EGF-R sites.

Passive immunotherapy using monoclonal antibodies against the EGF-R have been the object of multiple investigations and have demonstrated that the specific recognition of the receptor by the antibody inhibits the EGF binding and has an inhibitory effect on the mitogenic stimulation of malignant cells (Sato J D et al; (1987) Methods in Enzimology 148, 63–81). However, there is evidence that the murine origin of these antibodies produces a human anti-mouse antibody response.

The development of the hybridoma antibody technique by Kohler and Milstein revolutionized the discipline of immunochemistry and provided a new family of reagents with potential applications in clinical diagnosis and immunotherapy (Kohler G, Milstein C; (1975) Nature 256, 495–497). While it has become routine to produce mouse monoclonal antibodies (mAbs) for use in basic research and clinical diagnosis, it has been difficult to use these mAbs for in vivo immunotherapy because they have reduced half-life in humans, there is poor recognition of mouse antibody effector domains by the human immune system, and the foreign immunoglobulin can elicit an antiglobulin response (HAMA response) that may interfere with therapy.

The ability to genetically manipulate antibody genes and then express these altered genes by transfection techniques enables us to produce mAbs having more desirable properties than the existing hybridoma antibodies. Thus, genetic engineering can be used to enhance desired effector functions in antibody molecules and to decrease or eliminate undesired effector functions.

The use of recombinant DNA technology to clone antibody genes has provided an alternative wherein a murine mAb can be converted to a predominantly human form with the same antigen binding properties. In 1984, S L Morrison created mouse-human antibody molecules, of defined antigen-binding specificity, by taking the variable regions genes of mouse antibody producing myeloma cell lines, and joining them to human immunoglobulin constant regions (Morrison S L et al; (1984) PNAS USA 81, 6851–6855).

Other authors have attempted to build rodent antigen binding sites directly into human antibodies by transplanting only the antigen binding site, rather than the entire variable domain, from a murine antibody (Jones P T et al; (1986) Nature 321, 522–524; Verhoeven M et al; (1988) Science 239, 1534–1536). Some applications of this method have been developed (Rietchmann L et al; (1988) Nature 332, 323–327; Quee C et al; (1989) PNAS USA 86, 10029–10033), other authors have worked with reshaped antibodies, which included some murine residues in human FRs in order to recover the affinity for the original antigen (Tempest PR; (1991) Biotechnology 9, 266–272).

Orlandi R et al. (Proc Natl Acad Sci USA 86, 3833–3837, 1989) disclose the constant regions of the human gamma-1 heavy chain and the human kappa light chain, and suitable cloning vectors thereof.

DISCLOSURE OF THE INVENTION

The invention provides a chimeric and a humanized mAb which are directed to the EGF-R comprising, an antigen-binding site of non-human origin, and the constant regions of human origins (chimeric) and the framework regions ("FRs") of the variable regions and the constant regions of human origins may be, if necessary, modified in a way that the specificity of the binding to EGR-R can be conserved or restored.

The present invention can be used to characterize the hypervariable regions of the antigen-binding site of an antibody against the EGF-R and provide these CDRs within a humanized and chimeric mAb defined as above.

These antibodies can play a role as a therapeutic or diagnostic agent in order to combat tumors with high expression of EGF-R.

The present invention also provides chimeric and humanized antibodies specific for the EGF-R.

More specifically, the invention provides a chimeric monoclonal antibody comprising variable regions of non-human origin and constant regions of light and heavy chains of human origin, wherein the chimeric monoclonal antibody binds to human EGF-R and inhibits binding of EGF to EGF-R. According to a preferred embodiment of the chimeric monoclonal antibody, the variable regions of the antigen binding sites comprise the amino acid sequences shown in FIGS. 1a and 1b.

Further, the invention provides a humanized monoclonal antibody comprising antigen binding sites (CDRs) of non-human origin and the FRs of variable region and constant regions of light and heavy chains of human origin, wherein the humanized monoclonal antibody binds to human EGF-R and inhibits binding of EGF to EGF-R. According to a preferred embodiment of the humanized monoclonal antibody, the hypervariable regions of the antigen binding sites comprise the amino acid sequences underlined in FIG. 1 and FIG. 1b. Preferably, the FRs of the variable region which is not related to the antigen binding sites comprise the following amino acid sequences:

light chain:
  FR1: asp-ie-gln-met-thr-gln-ser-pro-ser-ser-leu-ser-ala-ser-val-gly-asp-arg-val-thr-ile-thr-cys (SEQ ID NO: 1),
  FR2: trp-tyr-gln-gln-thr-pro-gly-lys-ala-pro-lys-leu-leu-ile-tyr (SEQ ID NO: 2),
  FR3: gly-val-pro-ser-arg-phe-ser-gly-ser-gly-ser-gly-thr-asp-phe-thr-phe-thr-ile-ser-ser-leu-gln-pro-glu-asp-ile-ala-thr-tyr-tyr-cys (SEQ ID NO: 3),
  FR4: phe-gly-gln-gly-thr-lys-leu-gln-ile-thr-arg-glu (SEQ ID NO: 4),
  FR1: gln-val-gln-leu-gln-gln-ser-gly-ala-glu-val-lys-lys-pro-gly-ser-ser-val-lys-val-ser-cys-lys-ala-ser-gly-tyr-thr-phe-thr (SEQ ID NO: 5),
  FR2: trp-val-arg-gln-ala-pro-gly-gln-gly-leu-glu-trp-ile-gly (SEQ ID NO: 6),
  FR3: (arg,lys)-(val,ala)-thr-ile-thr-val-asp-glu-ser-(thr,ser)-(thr,asn)-thr-ala-tyr-met-glu-leu-ser-ser-leu-arg-ser-glu-asp-thr-ala-phe-tyr-phe-cys-(ala,thr)-arg (SEQ ID NO: 7),
  FR4: trp-gly-gln-gly-ser-thr-val-thr-val-ser-ser (SEQ ID NO: 8), and wherein the amino acids listed in brackets are alternatives.

The humanized monoclonal antibody may comprise a derivative of an amino acid sequence modified by amino acid substitution within the variable and constant regions wherein the biological function of specific binding to the antigen is preserved.

In a preferred embodiment of the humanized and chimeric monoclonal antibodies of the present invention, the constant region of the heavy chain comprises the amino acid sequence of a gamma-1 chain and the constant regions of the light chain comprise the amino acid sequences of a kappa chain of a human immunoglobulin. A purified humanized or chimeric monoclonal antibody which derives from murine mAb R3 is preferred.

The invention also includes a pharmaceutical composition comprising a chimeric or humanized monoclonal antibody as defined herein. Usually, the composition will also contain a pharmaceutically acceptable carrier.

The invention also includes in the use of a humanized or chimeric antibody, as defined herein, for the manufacture of a drug directed to tumors, and use of a humanized or chimeric antibody, as defined herein, for diagnostic localization and assessing tumor growth.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1a: Deduced amino acid sequence of VK of murine R3 antibody. CDRs are undelined.

FIG. 1b: Deduced amino acid sequence of VH of murine R3 antibody. CDRs are underlined. FIG. 2a: Amino acid sequence of murine and humanized VK containing mAb R3 CDRs.

FIG. 2b: Amino acid sequence of murine and humanized VH containing mAb R3 CDRs.

FIG. 3: Detection of binding of the chimeric and humanized R3 to EGF-R by RRA. Antigen binding activity was assayed in different concentrations of purified murine R3(+), chimeric R3 (*) and humanized (1) R3 (-.-) and plotted as CPM of bound $^{125}$1-EGF against log of the concentration of each antibody. (Concentration of IgG was quantitated by ELISA, see detailed description of the invention).

FIG. 5: Comparison of the amino acid sequences of reshaped humanized R3 heavy chain variable region. The CDRs are underlined.

Figure 4:
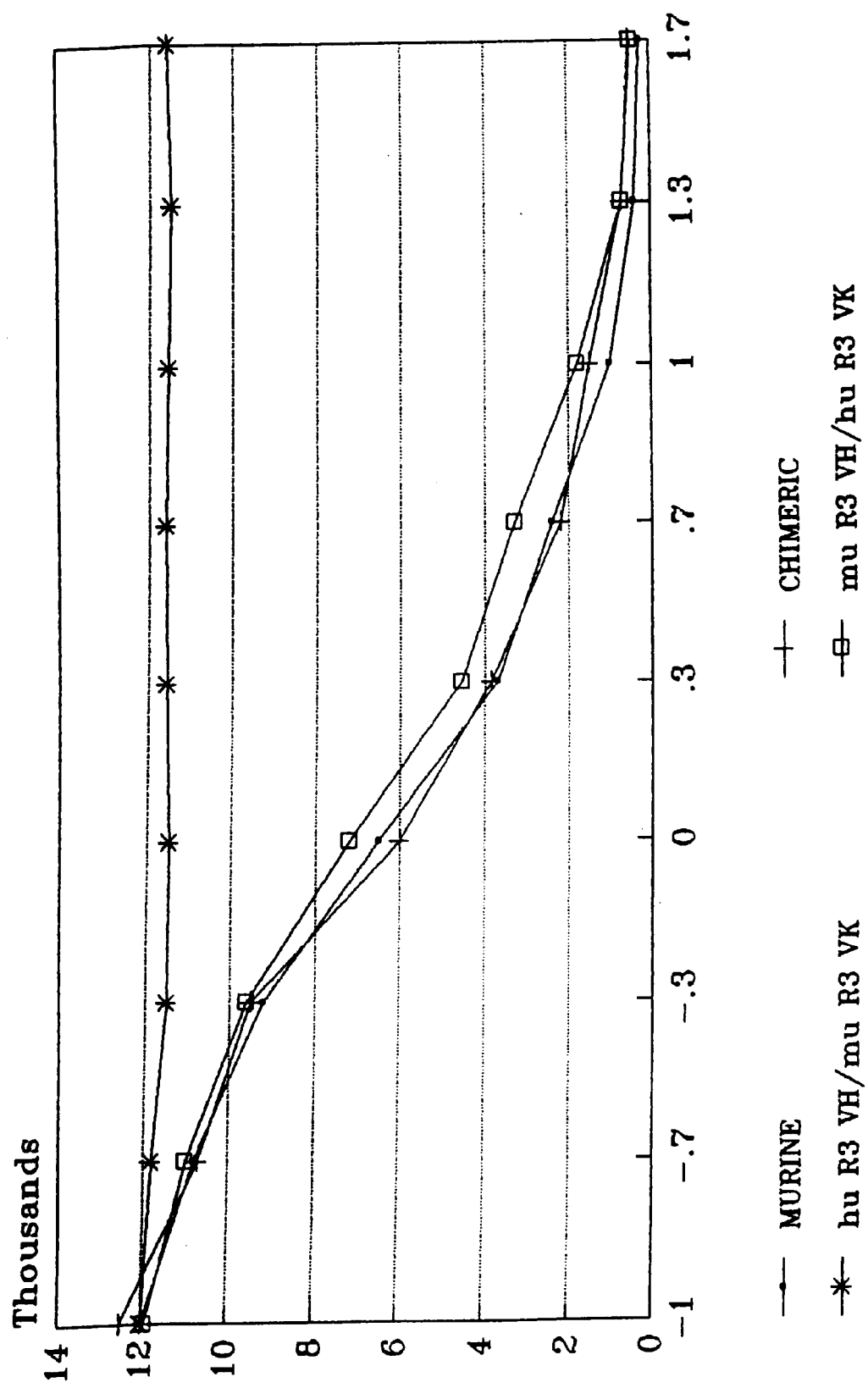
FIG. 4: Detection of binding of hybrids murine R3 VH/humanized R3 VK and humanized R3 VH/murine R3 VK. The antigen binding activity was assayed in dilutions concentrated supernatants from transfected NSO cells and plotted as cpm (membrane bound radioactivity) against log of the concentration of IgG estimated by ELISA, see experimental protocols.

DETAILED DESCRIPTION OF THE INVENTION cDNA Synthesis and Gene Amplification of Variable Region of R3

Cytoplasmic RNA was extracted from about $10^6$ hybridoma cells of R3 (IgG 2A), this antibody was obtained by us (Fernandez A et al; (1989) IFN y Biotecnologia 6(3), 289–298). The method used to extract RNA was described by Faloro et al: (Faloro J, Treisman R and Kemen R; (1989) Methods in Enzymology 65: 718–749).

The cDNA synthesis reaction mixture was done as described by Tempest et al. (Tempest P R, Bremner P, Lambert M, Taylor G, Furze J M, Carr F D J and Harris W J; (1991) Biotechnology 9: 266–271). Briefly, a 50 ul reaction mixture containing 5 ug of mRNA, 25 pmol of Vh or VK primer FOR, 250 uM of each dNTP, 10 mM DTT, 50 mM Tris-HCl (pH 8.3), 8 mM $MgCl_2$, 75 mM KCl and 15 units of RNAse inhibitor, was heated at 70° C., for 10 min and slowly cooled to 37° C. over a period of 30 min. Then, 100 units MLV reverse transcriptase (BRL) were added and the incubation at 37° C. continued for 1 hour.

The VH and VK cDNAs were amplified using the PCR as described by Orlandi et al (Orlandi R, Gussow D H, Jones P T and Winter G; (1989) Proc Natl Acad Sci USA 86: 3833–3837). For PCR amplification of VH, DNA/primers mixture consisted of 5 ul cDNA, 25 pmoles CG2AFOR and VH1BACK primers. For PCR amplification of VK, DNA/primers mixture consisted of 5 ul cDNA, 25 pmoles CK2FOR and VK10OBACK primers. To these mixtures were added 2.5 mM of each dNTP, 5 ul constituents of 10×buffer thermolase and 1 unit of Thermolase (IBI) in a final volume of 50 ul. Samples were subjected to 25 thermal cycles at 94° C., 30 sec; 50° C., 30 sec; 72° C., 1 min; and a last incubation for 5 min at 72° C. Amplified VH and VK DNA were purified on Prep A Gene purification kit (BioRad).

Cloning and Sequencing of Amplified cDNA

The purified VH and VK cDNA were cloned into M13-mp19 vector. Clones were sequenced by the dideoxy method using T7 DNA Pol (Pharmacia). We reamplified the cDNA by PCR using VH1BACK and VH1FOR primers for VH and VK3BACK and VK3FOR primers for VK. The amplified cDNAs were digested with PstI and BstEII for the VH gene or PvuII and BglII for the VK gene. The fragments were cloned into M13-VHPCR1 (digested with PstI and BstEII) or into M13-VKPCR1 (digested with PvuII and BclII). The M13VHPCR-R3 and M13VKPCR-R3 containing V gene inserts were identified directly by sequencing.

Construction of Chimeric Genes

The VH gene together with the Ig heavy chain promoter, appropriated splicing sites and signal peptide sequences were excised from M13 vectors by digestion with HindIII and BamHI and cloned into an expression vector (pSVgpt). A human IgG1 constant region (Takahashi N, Veda S, Obatu M, Nikaido T, Nakai S and Honjo T; (1982) Cell 29: 718–749), was then added as a BamHI fragment. The resultant construction was R3VH-pSVgpt. The construction of the R3VK-pSVhyg was essentially the same except that the gpt gene was replaced by the hygromycin resistance gene and a human Kappa chain constant region was added (Hieter P A, Max E E, Seidman J G, Maizel J V Jr and Leder P; (1980) Cell 22: 197–207).

Chimeric Antibody Expression

NSO cells were electroporated with 4 ug of R3VH-pSVgpt gamma 1 region and 8 ug R3VK-pSVhyg kappa constant region were linearized by digestion with PvuI. The DNAs were mixed together, ethanol precipitated and dissolved in 25 ul water. Approximately $10^7$ NSO cells were grown to semiconfluency, harvested by centrifugation and resuspended in 0.5 ml DMEN together with the digested DNA in an electroporation cuvette. After 5 minutes on ice, the cells were given a pulse of 170 volts and 960 uF (Gene-Pulser, Bio-Rad) and left in ice for a further 30 minutes. The cells were then put into 20 ml DMEN plus 10% fetal calf serum and allowed to recover for 48 hours. At this time the cells were distributed into a 96-well plate and selective medium applied (DMEN, 10% fetal calf serum, 0.8 ug/ml mycophenolic acid, 250 ug/ml xanthine). Transfected clones were visible with the naked eye 14 days later.

The presence of human antibody in the medium of wells containing transfected clones was measured by ELISA. Microtiter plate wells were coated with goat anti-human IgG (gamma chain specific) antibodies (Sera Lab). After washing with PBST (phosphate buffered saline containing 0.02% Tween 20, pH 7.5), 20 ul of culture medium from the wells containing transfectants was added to each microtiter well for 1 hour at 37° C. The wells were then emptied, washed with PBST and peroxidase-conjugated goat anti-human Kappa, light chain specific (Ser-Lab), were added and incubated at 37° C. for one hour. The wells were then emptied, washed with PBST and substrated buffer containing o-phenylediamine added. Reactions were stopped after a few minutes by the addition of sulphuric acid and absorbance at 492 nm was measured.

Transplantation of CDRs into Human Frameworks

The construction of the first version of humanized of R3-huVH(a) and R3-huVK was carried out using a CDR grafting approach similar to that described by Kunkel et al. (Kunkel T A; (1985) Proc Natl Aca Sci USA 82, 488; Kunkel T A; (1987) Methods in Enzymology 155, 166). Briefly: To 0.5 ug of VH or VK single stranded Uracil DNA in M13 VH or VK PCR vectors (coding for the human Eu VH region sequence and human REI VK region sequence) were added ten pmoles of VH or VK phosphorylated oligonucleotides encoding the mouse CDRs sequences. Primers were annealed on the template by heating to 70° C. and slowly cooled to 37° C. After site-directed mutagenesis, the DNA was transformed into competent *E. coli* TG1 cells. Single strand DNA was prepared from individual plaques and sequenced. If only single or double mutants were obtained, then these were subjected to further rounds of mutagenesis using the appropriate oligonucleotides until the triple CDR mutants were obtained.

Further versions of reshaped human R3VH were constructed using PCR mutagenesis (Kammann M, Laufs J, Schell J and Gronenbom B; (1989) PNAS USA 86, 4220–4224), using the oligonucleotides described in example 5.

Cloning and Expression of Humanized R3 Antibody into NSO Cells

After CDR-grafting, the HindIII-BamHI fragment carrying the R3 humanized VH and R3 humanized VK genes were recloned in expression vectors, yielding the plasmids R3HuVH(1–7)-pSVgpt gamma1 and HuR3VK-pSVhyg kappa constant region. Vectors were linearized with PvuI, and humanized expression was done like chimaeric expression into NSO cells.

Molecular Modeling of mAb R3 VK and VH

A model of the variable regions of mouse mAb R3 was built using the molecular modeling program QUANTA/CHARm 4.0 (Molecular Simulations Inc., 1994), running on a 150 MHz Silicon Graphics Indigo Extreme workstation. The VK and VH frameworks were built separately from Fab 26-10 (Jeffrey P D, Strong R K, Sieker L C, Chang C Y, Campbell R L, Petsko G A, Haber E, Margolies M N and Sheriff S; (1993) PNAS USA 90, 10310) and Fab 36-71 (Strong R K, Campbell R L, Rose D R, Petsko G A, Sharon J and Margolies M N; (1993) Biochemistry 30, 3739), respectively, Fab 26-10 and mAb R3 have 92% homology in the VK frameworks and 88% homology in the whole VK region. The VH frameworks of Fab 36-71 and R3 mAb have 85% homology.

Coordinates were taken from the Brookhaven Protein Data Bank (entries 11GI and 6FAB). The frameworks of Fab 36-71 were fitted to the frameworks of Fab 26-10, matching only those residues that have been found to be often involved in the interface between the light and heavy variable regions (Chotia C, Novotny J, Bruccolery R and Karplus M; (1985) J Mol Biol 186, 651). The VH domain of Fab 26-10 and the VK domain of Fab 36-71 were then deleted leaving the needed hybrid. Side-chain replacements were performed following the maximum overlap procedure (Snow M E and Amzel L M; (1986) Proteins 1, 267), and comparing, where possible, with other crystal structures.

The hypervariable regions of the R3-Variable Light (VL) domain (L1, L2 and L3) were built retaining the same main-chain conformations as in Fab 26-10, since the corresponding CDRs in both antibodies are highly homologous and belong to the same canonical structural groups (Chotia C, Lesk A M, Tramontano A, Levitt M, Smith-Gill S J, Air G, Sherii S, Padlan E A, Davies D, Tulip W R, Colman P M, Spinelli S, Alzari P M and Poljak R J; (1989) Nature 342, 877). In the VH domain of mAb R3, CDR H1 belongs to canonical structural group 1, as in Fab 36-71, so the main-chain torsion angles of the parent molecule were kept. CDR H2 corresponds to canonical structural group 2 and the main-chain conformation for this loop was taken from the Fv fragment 4D5 (entry 1FVC), which was selected among other highly resolved structures because of the good matching of its H2 loop base with the framework of Fab 36-71. For all the above mentioned loops, comparisons with other CDRs from the Data Bank were made to orient the side chains.

To model CDR H3, which in mAb R3 was 14 amino acids long, a high temperature molecular dynamics was used for conformational sampling (Bruccoleri R E and Karplus M; (1990) Biopolymers 29, 1847). First, the whole structure without CDR H3 was subjected to an energy minimization keeping residues H-94 and H-103 fixed and using harmonic constraints of 10 Kcal/(mole atom $A^2$) for main chain atoms. Then a loop was constructed with an arbitrary conformation starting from the two previously fixed amino acids. Those residues close to the framework were placed taking into consideration other crystal structures and the top part of the loop was built with an extended conformation avoiding strong steric interactions with the rest of the molecule. For the next modeling steps only CDR H3 and the neighboring side chains within a distance of $5A^0$ were permitted to move. An energy minimization was first carried out and then a molecular dynamics at 800K was run for 150 picoseconds. The time step for the run was set to 0.001 picosecond and coordinates were saved every 100 steps. The 120 lowest energy conformations from the dynamics run were extracted and subjected to an energy minimization in which all atoms in the structure were allowed to move. Several low-energy conformations were obtained and the one with the lowest energy was used in the subsequent analyses. Differences between murine and humanized variants of R3 antibody were individually modeled to investigate their possible influence on CDR conformation.

EGF Receptor Radioligand Competition Assays

The determination of the apparent inhibition constants (Ki) of the $^{125}$I-EGF binding to its receptor by the anti EGF-R mAb was performed by homogeneous Radio Receptor Analysis (RRA) with human placenta microsomal fraction. (Macias A, Perez R, Lage A; (1985) Interferon y Biotecnologia 2: 115–127). The affinity constant of the antigen antibody reaction was also estimated by a competitive RRA but using mAb $^{125}$I-R3 as the radiolabeled probe.

Materials

Recombinant Human Epidermal Growth Factor (HEGF) was obtained from the Center of Genetic Engineering and Biotechnology, Havana, Cuba. $^{125}$I-hEGF was radioiodinated by the chloramine-T method (specific activity 150–200 uCi/ug). Murine hybridoma cell line R3 was obtained by us (European Patent Application No 93202428.4). Rat myeloma NSO is a non-Ig secreting cell line and was grown in Dulbecco's modified Eagles medium (DMEN) containing 10% fetal calf serum. Vectors M13VHPCR1, M13VKPCR1, pSVgpt and pSVhyg have been described in detail (Orlandi R, Gussow D H, Jones P T and Winter G; (1989) Proc Natl Acad Sci USA 86: 3833–3837) and were obtained from Greg Winter, MRC Laboratory of Molecular Biology, Cambridge, UK. Oligonucleotides were synthesized using an Applied Biosystems 381 DNA synthesizer.

Pharmaceutical Compositions

With respect to the formulation of suitable compositions for administration to patients in need of treatment, the monoclonal antibodies according to the invention may be admixed or combined with pharmaceutically acceptable carriers known per se, dependent upon the chosen route of administration. There are no particular limitations to the modes of application of the invention, and the choice of suitable administration routes and suitable compositions belong to the routine skills of persons skilled in the art.

Although other forms of administration are possible as well, a preferred administration form would be a solution for injection, in particular for intravenous or intraarterial injection. Usually, a suitable pharmaceutical composition for injection may comprise a buffer (e.g. acetate, phosphate or citrate buffer), a surfactant (e.g. polysorbate), optionally a stabilizer agent (e.g. human albumine), etc. Persons skilled in the art know, or can easily determine, other possibilities.

Similarly, persons skilled in the art have the ability to determine the best concentrations and proportions of the various components, administration dose and frequency, etc. For example, a suitable solution for injection will usually contain from about 1 to about 20, preferably 5–10 mg antibody per ml. The dose to be administered could, for example, be from about 0.1 to about 20, preferably 1–5 mg/kg body weight, and administration could be once per day, or three times per week, or whatever the physician thinks best.

EXAMPLE 1

Molecular Cloning Sequencing

VH and VK were amplified using PCR. The specific oligonucleotides used as primers were:
For the heavy chain variable region:
CG2AFOR (5' GGAAGCTTAGACCGATGGGGCCTGT-TGTTTTG 3') (SEQ ID NO: 9);
VH1BACK (5' AGGT(G/C)(A/C)A(A/G)CTGCAG(G/C)AGTC(A/T)GG 3') (SEQ ID NO: 10).
For the light chain variable region:
CK2FOR (5' GAAGCTTGAAGATGGATACAGTTGGTG-CAGC 3') (SEQ ID NO: 11);
VK10BACK (5' TTGAATTCCAGTGATGTTTTGATGAC-CCA 3') (SEQ ID NO: 12).

The purified VH and VK cDNA were cloned into M13 vector. Twelve independent clones were sequenced by the dideoxy method using T7 DNA Pol (Pharmacia). In FIGS. 1a and 1b, you can see the variable region sequences of the murine R3 mAb. The VH sequence is most closely related to kabat subgroup VH IIB and the VK to kabat subgroup II.

EXAMPLE 2

Construction of Chimeric Genes

We reamplified the cDNA by PCR using the following oligonucleotides as primers:
For VH:
VH1BACK (5' AGGT(G/C)(A/C)A(A/G)CTGCAG(G/C)AGTC(A/T)GG 3') (SEQ ID NO: 10);
VHb 1FOR (5' TGAGGAGACGGTGACCGTGGTCCCT-TGGCCCCAG 3') (SEQ ID NO: 13).
For Vk:
VK3BACK (5' GACATTCAGCTGACCCA 3') (SEQ ID NO: 14);
VK3FOR (5' GTTAGATCTCCAGTTTGGTGCT 3') (SEQ ID NO: 15).

The amplified cDNAs were digested with PstI and BstEII for the VH gene or PvuII and BglII for the VK gene. The fragments were cloned into M13-VHPCR1 (digested with PstI and BstEII) or into M13-VKPCR1 (digested with PvuII and BclI). Details of vectors (Orlandi R et al; Proc Natl Acad Sci USA 86: 3833–3837, 1989). The M13VHPCR-R3 and M13VKPCR-R3 containing V gene inserts were identified directly by sequencing.

The VH gene together with the Ig heavy chain promoter, appropriated splicing sites and signal peptide sequences were excised from M13 vectors by digestion with HindIII and BamHI and cloned into an expression vector (pSVgpt). A human IgG1 constant region (Takahashi N et al; Cell 29: 718–749, 1982) was then added as a BamHI fragment. The resultant construction was R3VH-pSVgpt. The construction of the R3VK-pSVhyg was essentially the same, except that the gpt gene was replaced by the hygromycin resistance gene and a human Kappa chain constant region was added (Hieter PA et al; Cell 22: 197–207, 1980).

EXAMPLE 3

Transplantation of Murine CDRs of R3 into Human FRs

We compared murine light and heavy chains variable regions of R3 with variable regions sequences of human immunoglobulins.

The murine R3 heavy chain variable region has 63.4% of homology with human subgroup VHI and the R3 light chain variable region has 63.7% of homology with human subgroup VKI. The human FRs chosen were derived of the human immunoglobulin REI for the light chain and the human immunoglobulin EU for the heavy chain.

The construction of the first version of the humanized R3 heavy chain and humanized R3 light chain was carried out using CDR grafting approach as described herein.

Oligonucleotides were designed which consisted of DNA sequences coding for each end by 12 bases of DNA complementary to the DNA sequences coding for the adjacent FRs of human Eu for Vh and human REI for VK. The oligonucleotides designed were:
For the CDR1 of the light chain:
5' TCTAGATCAGTCTTGTAACATGTATCAT-TACCTTTGTGGATAAATCTG 3' (SEQ ID NO: 16).
We did not use oligonucleotides for the CDR2 because REI human CDR2 is identical to R3 CDR2.
For the CDR3 of the light chain:
5' GATGACGAAAGTTATCAAGTGTACAAGGGACCTG 3' (SEQ ID NO: 17).
For the CDR1 of the heavy chain:
5' ATGTGGAAGTGGTTAATAATATA-GATAACCCACTCTGTC 3' (SEQ ID NO: 18).
For the CDR2 of the heavy chain:
5' ACTACCTACCCTCCCTATTTGGGGTG-GAGACCTCCCTCATTGAAATTACTTTTCA GTTCT-GTTCTCACTGTTAA 3' (SEQ ID NO: 19).
For the CDR 3 of the heavy chain:
5' AAAACACGTTCTGTCCCGAACAC-CAAGCTGTCACTGCCTGCCCCGAAACTGAAG 3' (SEQ ID NO: 20).

EXAMPLE 4

Expression of Chimeric and Humanized in NSO Cells

NSO cells were electroporated with 4 ug of murine or humanized R3 VH-CMMAR gamma 1 region and 8 ug of murine or humanized R3VK-CMMARhyg kappa constant region were linearized by digestion with PvuI. The DNAs were mixed together, ethanol precipitated and dissolved in 25 ul water. Approximately $10^7$ NSO cells were grown to semiconfluency, harvested by centrifugation and resuspended in 0.5 ml DMEN together with the digested DNA in an electroporation cuvette. After 5 minutes on ice, the cells were given a pulse of 170 volts and 960 uF (Gene-Pulser, Bio-Rad) and left in ice for a further 30 minutes. The cells were put into 20 ml DMEN plus 10% fetal calf serum and allowed to recover for 48 hours. At this time the cells were distributed into 96-well plate and selective medium applied (DMEN, 10% fetal calf serum, 0.8 ug/ml mycophenolic acid, 250 ug/ml xanthine). Transfected clones were visible with the naked eye 14 days later.

The presence of human antibody in the medium of wells containing transfected clones was measured by ELISA. Microtiter plate wells were coated with goat anti-human IgG (gamma chain specific) antibodies (Sera Lab). After washing with PBST (phosphate buffered saline containing 0.02% Tween 20, pH 7.5), 20 ul of culture medium from the wells containing transfectants was added to each microtiter well for 1 hour at 37° C. The wells were then emptied, washed with PBST and peroxidase-conjugated goat anti-human Kappa, light chain specific (Sera-Lab), were added and incubated at 37° C. for one hour. The wells were then emptied, washed with PBST and substrated buffer containing o-phenylenediamine added. Reactions were stopped after a few minutes by the addition of sulphuric acid and absorbance at 492 nm was measured.

In FIG. 3 the chimeric and murine R3 antibody bind to the EGF-R with the same affinity (tested in RRA), and the first version of humanized R3 antibody did not bind to the EGF-R.

EXAMPLE 5

Construction of Different Versions of Humanized R3 Antibodies, with Some Murine Residues in the FRs Regions The introduction of some murine residues in the human FRs was necessary because the first version of humanized R3 antibodies that we constructed did not bind to the antigen.

We constructed hybrids between murine R3VH/humanized R3VK and humanized R3VH/murine R3VK. FIG. 4 shows that the hybrid murine R3VH/humanized R3VK binds to the EGF-R with the same affinity as the original murine R3.

Humanized R3huVk retained all the Vernier's residues of murine R3VK. This fact may explain why the humanizing procedure did not affect the binding capability of the kappa chain.

Nevertheless humanized R3VH/murine R3VK did not work. This result suggested to us that we had to include murine residues into human FRs of the heavy chain, for the recovery of the binding to the antigen of this antibody.

Then, other versions of the reshaped humanized heavy chains were constructed by PCR mutagenesis. In these new versions we tried to keep the Vernier's zone intact, recommending changes in the position 66, 67, 75, 76 and 93 (Kabat numbering) in the FRs regions.

The oligonucleotides designed to get the reshaped R3VH-K66A67 were:
Top strand:
5' GAAAAGTTCAAGACAAAAGCGACAAT-TACGGTAGAC 3' (SEQ ID NO: 21).
Lower strand:
5' GTCTACCGTAATTGTCGCTTTTGTCT-TGAACTTGAACTTTTC 3' (SEQ ID NO: 22).
The oligonucleotides designed to get the reshaped R3VH-S75T76 were:
Top strand:
5' GTAGACGAGAGCAGCACCACGGCGTACATG 3' (SEQ ID NO: 23).
Lower strand:
5° CATGTACGCCGTGGTGCTGCTCTCGTCTAC 3' (SEQ ID NO: 24).
The oligonucleotides designed to get the reshaped R3VH-T93 were:
Top strand:
5' TTCTATTTTTGTACAAGACAGGGCTTG 3' (SEQ ID NO: 25).
Lower strand:
5° CAAGCCCTGTCTTGTACAAAAATAGAA 3' (SEQ ID NO: 26).

EXAMPLE 6

Molecular Modeling of mAb R3 VK and VH

A model of the variable regions of mouse mAb R3 was built using the molecular modeling program QUANTA/CHARm 4.0 (Molecular Simulations Inc, 1994), running on a 150 MHz Silicon Graphics Indigo Extreme workstation.

Differences between murine and humanized variants of R3 antibody were individually modeled to investigate their possible influence on CDR conformation.

Figure 6:
FIG. 6: Molecular Model of the Variable region of murine mAb R3. The binding site is at the top and the molecule has been slightly rotated clockwise around a vertical axis so that VH domain approaches the viewer. The VL framework is light blue and the VH framework is pink. The corresponding CDRs are marked in dark blue and red. Side chains of residue Ser 75, Thr 76 and Thr 93 (with polar hydrogen atoms included) are shown in green. The side chain of the Phe 100f is shown in red.

Heavy chain variable region residues at positions 66, 67, 75, 76 and 93, (Kabat numbering) which had been changed in humanized R3huVH (FIG. 6), are close to the hypervariable loops and therefore may influence the CDR conformations. Both our experimental results and the modeling studies suggest that only Thr76 and Thr93 (Kabat numbering) are critical for binding affinity.

A molecular model of the murine R3 heavy chain variable regions was constructed to analyze the possible effects of these mutations. Residue 93 was located just below CDR H3, close to Phe100f(Kabat numbering) (FIG. 6), and replacing Thr with a smaller amino acid like Ala may provoke some rearrangements of the neighboring side chains and modify the overall conformation of the H3 loop.

THR 76 is close to CDR H2 (FIG. 2) and the introduction of the larger Asn residue at this position could lead to hydrogen-bonding interactions with the backbone of CDR H1. Moreover, residue 76 is accessible from the top of the variable region and could be directly involved in the binding to EGF-R. The substitution Ser75-Thr (Kabat numbering) alone did not seem to have any influence, but taken together with mutation at position 76, could be important. The changes Lys66-Arg and Ala67-Val (Kabat numbering) did not appear to affect the structure, but since they had been found to have some influence in the functional binding of reshaped mAb 425 (Kettleborough C, Saldanha J, Heath V J, Morrison C J and Bending M M; (1991) Protein Engineering 4, 773–783), we decided to make substitutions at these positions as well.

Humanized R3huVK retained all the Vernier's residues of murine R3VK. This fact may explain why the humanizing procedure did not affect the binding capability of the kappa chain.

Figure 7:
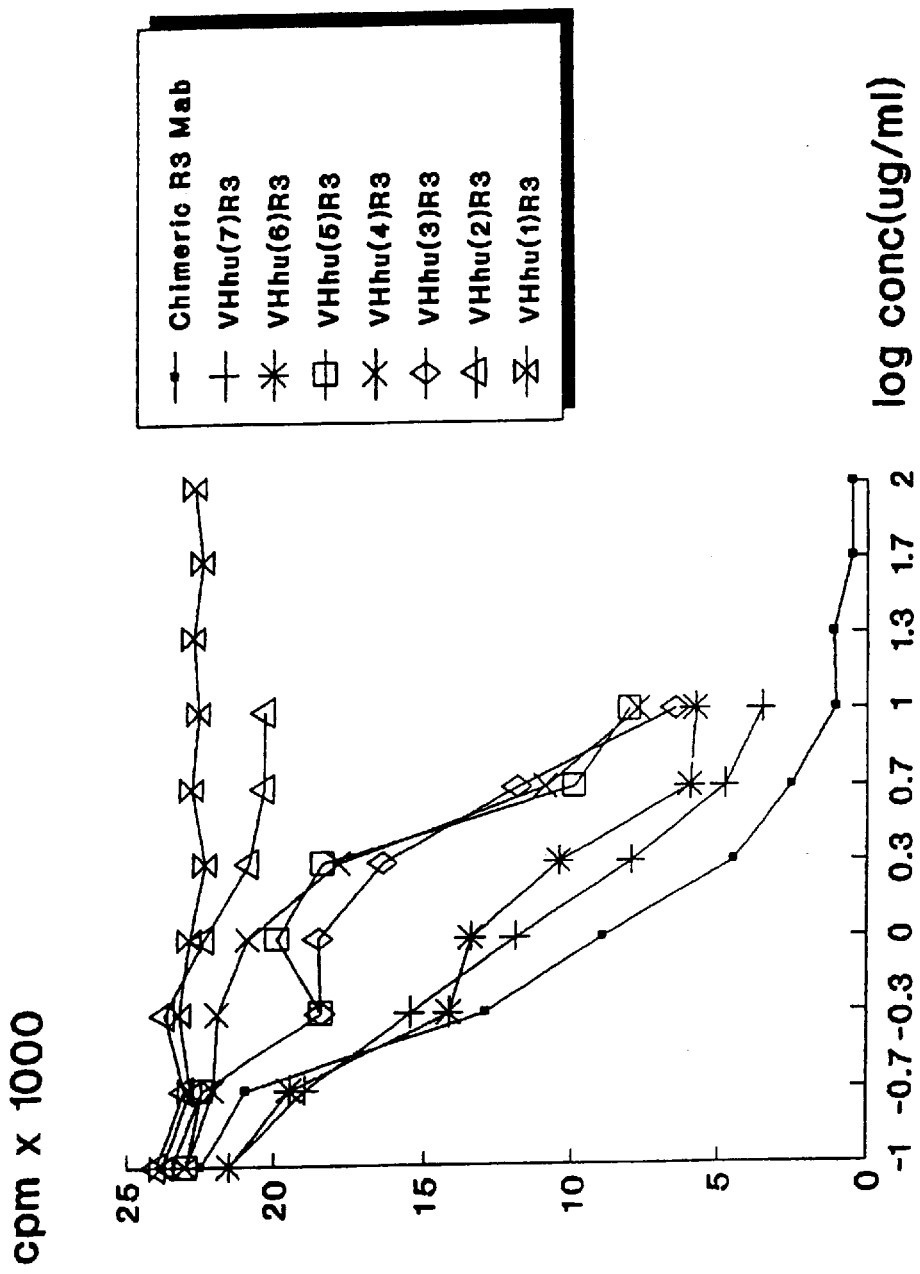
FIG. 7: Detection of binding of the different reshaped mAb R3 to EGF-R by RRA. Antigen binding activity was assayed in dilutions concentrated supernatants from transfected NSO cells and plotted as cpm (membrane bound radioactivity) against log of the concentration of IgG estimated by ELISA, see experimental protocols. All versions of reshaped human VH regions were cotransfected with huVKR3 and are represented in the figure.

Reshaped R3 hu VH antibodies containing either S75/T76 or T93 (Kabat numbering) recovered partially the binding capacity, whereas those constructs containing both of them retained full binding activity (FIG. 7).

EXAMPLE 7

EGF Receptor Radioligand Competition Assays

The determination of the affinity constant of the $^{125}$-EGF binding to its receptor by murine R3 chimeric and humanized antibodies was performed by an homogeneous Radio Receptor Analysis (RRA) with human placenta microsomal fraction (Macias A et al; Interferon y Biotecnologia 2: 115–127, 1985).

These different versions of chimeric and humanized antibodies were assayed, using this technique, for its ability to bind to EGF-R (FIG. 7). The different versions of reshaped human VH regions result in a wide range of levels of antigen binding (FIG. 7). Versions 6 and 7 have the same affinity as original murine antibody, these versions with highest levels of binding were followed of versions 3, 4 and 5 and then followed by version 2.

Based on these results, it is possible to comment on the relative contributions individual residues in the FRs make to antigen binding. The 75 and 76 changes are, together with 93 (all Kabat numbering) very important to the binding, while the introduction of changes at positions 66 and 67 (Kabat numbering) fail to produce significant antigen binding.

EXAMPLE 8

Immunization of *Cercopithecus aethiops* Monkeys with the Murine, Chimeric and VH Mutant Antibodies Three treatment groups with two *Cercopithecus aethiops* monkeys in each group were immunized as follows: 1.

Murine R3 monoclonal antibody (2 mg) with 5 mg of aluminum hydroxide as adjuvant; 2. Chimeric R3 antibody (2 mg) with 5 mg of aluminum hydroxide as adjuvant; and 3. Humanized (version 6) R3 antibody (2 mg) with 5 mg of aluminum hydroxide as adjuvant. All the groups were immunized intradermically on weeks 1, 3, 5, and 7. Starting on week one, blood was collected from all the groups weekly.

The serum obtained and the titer of antibodies against EGF-R was determined by an ELISA technique.

Costar plates (Inc, high binding) were coated with murine R3 monoclonal antibody at a concentration of 10 ug/ml in bicarbonate buffer (pH 9.6) and incubated overnight. After, the plates were washed with PBST and blocked with the same buffer containing 1% BSA for one hour at room temperature.

The washing step was repeated and 50 ul/well of the different serum dilutions were added. After incubating for 2 hours at 37° C., the plates were washed again and incubated for 1 hour at 37° C. with alkaline phosphated conjugated goat anti-human total or anti-human IgG Fc region specific antiserum (Sigma, Inc). After washing with PBST, the wells were incubated with 50 ul of substrate buffer (1 mg/ml of p-nitrophenylphosphate diluted in diethanolamine buffer (pH 9.8) and absorbance at 405 nm was read with an ELISA reader (Organon Teknika, Inc).

Figure 8:
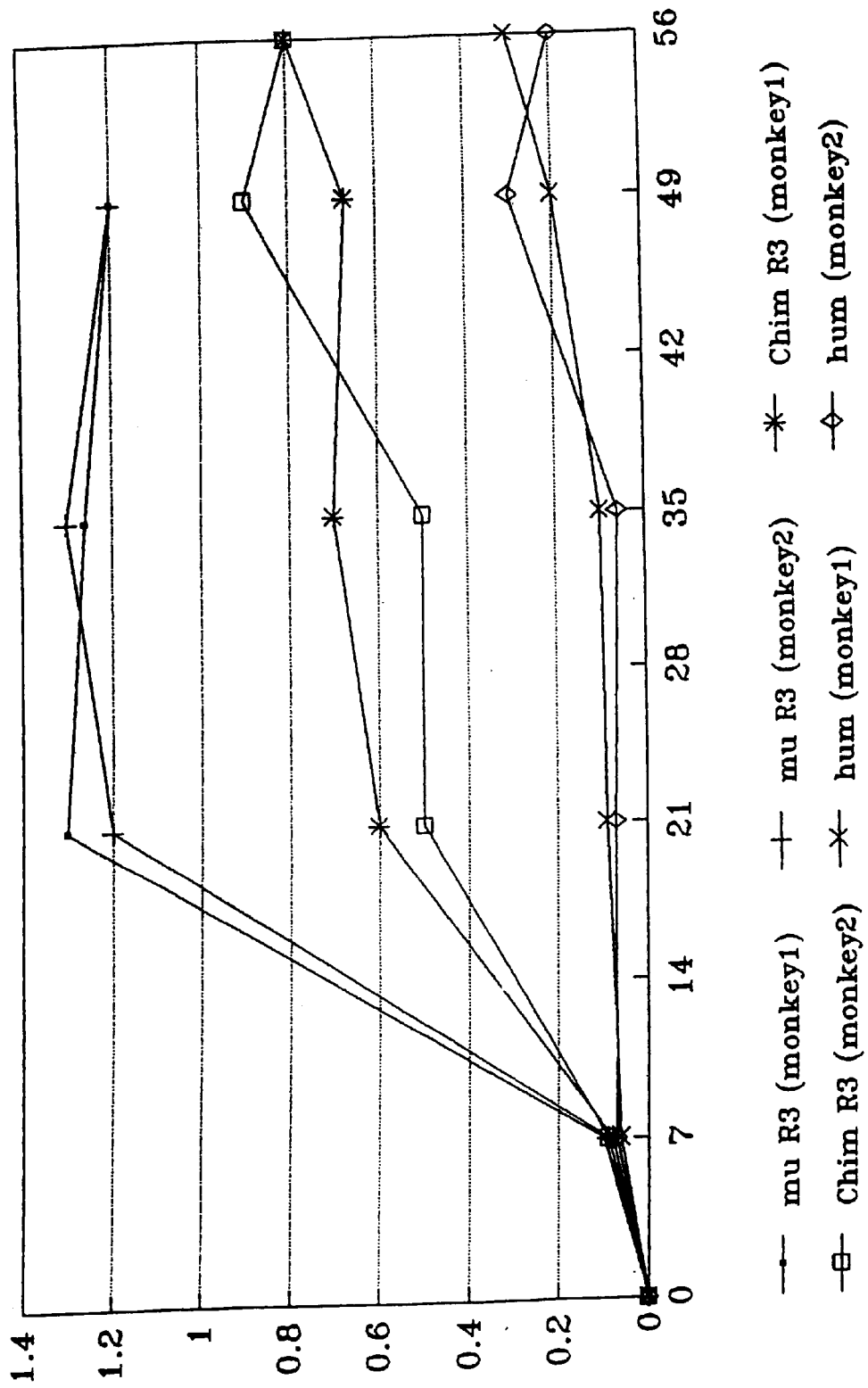
FIG. 8: Immunogenicity in monkeys of R3 murine mAb and different recombinant versions. *Cercopithecus aethiops* monkeys were immunized intradermically at 15 days intervals with 2 mg of the different mAbs versions using aluminum hydroxide as adjuvant. The detection of monkey IgG against the different versions of R3 mAb was tested in the sera of the animals using an indirect ELISA.

A high IgG response to murine R3 antibody was obtained when this antibody was used as immunogen. A lower but still measurable IgG response (1/10000) to the murine R3 antibody was obtained when monkeys were immunized with the chimeric antibody, contrary to the results obtained with the humanized (version 6) (FIG. 8). With the humanized antibody no response was measurable after 3 immunizations.

DEPOSIT

The cell line hr-R3 expressing the antibody was deposited pursuant to the Budapest Treaty with European Collection of Animal Cell Cultures, Centre for Applied Microbiology and Research Microbiological, Porton Down, Salisbury Wiltshire SP4, OJG, United Kingdom on Nov. 10, 1995, and obtained deposit number 9511 10101.

What is claimed is:

1. A monoclonal antibody which specifically binds to epidermal growth factor receptor (EGF-R), the monoclonal antibody comprising a chimeric antibody including variable regions of non-human origin and constant regions of light and heavy chains, said constant region being of human origin, the chimeric antibody including an amino acid sequence shown in SEQ ID NO: 7 wherein the variable regions of antigen binding sites include amino acid substitutions at one of positions 10, 11 and 31 as shown in SEQ ID NO: 7, wherein the biological function of specific binding to said EGF-R is preserved.

2. A monoclonal antibody which specifically binds to epidermal growth factor receptor (EGF-R), the monoclonal antibody comprising a humanized antibody including complementary determining regions of non-human origin, variable regions having framework regions (FRs) of human origin and constant regions of light and heavy chains, said constant region being of human origin, the FRs including an amino acid sequence shown in SEQ ID NO: 7 wherein the FRs include amino acid substitutions at one of positions 10, 11 and 31 as shown in SEQ ID NO: 7, wherein the biological function of specific binding to said EGF-R is preserved.

3. A hybridoma cell line identified as European Collection of Cell Cultures No. 951110101.

4. A monoclonal antibody obtained by a hybridoma cell line of claim 3.

5. A pharmaceutical composition comprising the antibody according to claim 1 in admixture with at pharmaceutically acceptable carrier.

6. A pharmaceutical composition comprising the antibody according to claim 2 in admixture with a pharmaceutically acceptable carrier.

7. The monoclonal antibody of claim 1, further including an amino acid substitution at one of positions 1 and 2 of SEQ ID NO: 7.

8. The monoclonal antibody of claim 1, wherein amino acid substitutions are made at positions 10, 11 and 31 of SEQ ID NO: 7.

9. The monoclonal antibody of claim 7, wherein amino acid substitutions are made at positions 1, 2, 10, 11 and 31 of SEQ ID NO: 7.

10. The monoclonal antibody of claim 2, further including an amino acid substitution at either position 1 or 2 of SEQ ID NO: 7.

11. The monoclonal antibody of claim 2, wherein amino acid substitutions are made at positions 10, 11 and 31 of SEQ ID NO: 7.

12. The monoclonal antibody of claim 10, wherein amino acid substitutions are made at positions 1, 2, 10, 11 and 31 of SEQ ID NO: 7.

* * * * *

SEQUENCE LISTING

<160> NUMBER OF SEQ ID NOS: 36

<210> SEQ ID NO 1
<211> LENGTH: 23
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 2
<211> LENGTH: 15
<212> TYPE: PRT
<213> ORGANISM: Homo sapiens

<400> SEQUENCE: 2

Trp Tyr Gln Gln Thr Pro Gly Lys Ala Pro Lys Leu Leu Ile Tyr
1               5                   10                  15

<210> SEQ ID NO 3
<211> LENGTH: 32
<212> TYPE: PRT
<213> ORGANISM: Homo sapiens

<400> SEQUENCE: 3

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 4
<211> LENGTH: 12
<212> TYPE: PRT
<213> ORGANISM: Homo sapiens

<400> SEQUENCE: 4

```
Phe Gly Gln Gly Thr Lys Leu Gln Ile Thr Arg Glu
1               5                   10

<210> SEQ ID NO 5
<211> LENGTH: 30
<212> TYPE: PRT
<213> ORGANISM: Homo sapiens

<400> SEQUENCE: 5

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 6
<211> LENGTH: 14
<212> TYPE: PRT
<213> ORGANISM: Homo sapiens

<400> SEQUENCE: 6

Trp Val Arg Gln Ala Pro Gly Gln Gly Leu Glu Trp Ile Gly
1               5                   10

<210> SEQ ID NO 7
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is either Arg or Lys
<220> FEATURE:
<221> NAME/KEY: MISC_FEATURE
<222> LOCATION: (2)..(2)
<223> OTHER INFORMATION: X is either Val or Ala
<220> FEATURE:
<221> NAME/KEY: MISC_FEATURE
<222> LOCATION: (10)..(10)
<223> OTHER INFORMATION: X is either Thr or Ser
<220> FEATURE:
<221> NAME/KEY: MISC_FEATURE
<222> LOCATION: (11)..(11)
<223> OTHER INFORMATION: X is either Thr or Asn
<220> FEATURE:
<221> NAME/KEY: MISC_FEATURE
<222> LOCATION: (31)..(31)
<223> OTHER INFORMATION: X is either Ala or Thr

<400> SEQUENCE: 7

Xaa Xaa Thr Ile Thr Val Asp Glu Ser Xaa Xaa Thr Ala Tyr Met Glu
1               5                   10                  15

Leu Ser Ser Leu Arg Ser Glu Asp Thr Ala Phe Tyr Phe Cys Xaa Arg
            20                  25                  30

<210> SEQ ID NO 8
<211> LENGTH: 11
<212> TYPE: PRT
<213> ORGANISM: Homo sapiens

<400> SEQUENCE: 8

Trp Gly Gln Gly Ser Thr Val Thr Val Ser Ser
1               5                   10

<210> SEQ ID NO 9
<211> LENGTH: 32
<212> TYPE: DNA
<213> ORGANISM: Artificial Sequence
<220> FEATURE:
```

```
<223> OTHER INFORMATION: oligonucleotide primer

<400> SEQUENCE: 9
ggaagcttag accgatgggg cctgttgttt tg                              32

<210> SEQ ID NO 10
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 10
aggtsmadct gcagsagtcw gg                                         22

<210> SEQ ID NO 11
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 11
ggaagcttga agatggatac agttggtgca gc                              32

<210> SEQ ID NO 12
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 12
ttgaattcca gtgatgtttt gatgaccca                                  29

<210> SEQ ID NO 13
<211> LENGTH: 34
<212> TYPE: DNA
<213> ORGANISM: Artificial Sequence
<220> FEATURE:
<223> OTHER INFORMATION: oligonucleotide sequence

<400> SEQUENCE: 13
tgaggagacg gtgaccgtgg tcccttggcc ccag                            34

<210> SEQ ID NO 14
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 14
gacattcagc tgaccca                                               17

<210> SEQ ID NO 15
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 15
gttagatctc cagtttggtg ct                                         22
```

<210> SEQ ID NO 16
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 16
tctagatcag tcttgtaaca tgtatcatta cctttgtgga taaatctg    48

<210> SEQ ID NO 17
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 17
gatgacgaaa gttatcaagt gtacaaggga cctg    34

<210> SEQ ID NO 18
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 18
atgtggaagt ggttaataat atagataacc cactctgtc    39

<210> SEQ ID NO 19
<211> LENGTH: 74
<212> TYPE: DNA
<213> ORGANISM: Artificial Sequence
<220> FEATURE:
<223> OTHER INFORMATION: oligonucleotide primer

<400> SEQUENCE: 19
actacctacc ctccctattt ggggtggaga cctccctcat tgaaattact tttcagttct    60
gttctcactg ttaa    74

<210> SEQ ID NO 20
<211> LENGTH: 54
<212> TYPE: DNA
<213> ORGANISM: Artificial Sequence
<220> FEATURE:
<223> OTHER INFORMATION: oligonucleotide primer

<400> SEQUENCE: 20
aaaacacgtt ctgtcccgaa caccaagctg tcactgcctg ccccgaaact gaag    54

<210> SEQ ID NO 21
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 21
gaaaagttca agacaaaagc gacaattacg gtagac    36

<210> SEQ ID NO 22
<211> LENGTH: 42
<212> TYPE: DNA
<213> ORGANISM: Artificial Sequence
<220> FEATURE:

<223> OTHER INFORMATION: oligonucleotide primer

<400> SEQUENCE: 22
gtctaccgta attgtcgctt ttgtcttgaa cttgaactttt tc          42

<210> SEQ ID NO 23
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 23
gtagacgaga gcagcaccac ggcgtacatg          30

<210> SEQ ID NO 24
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 24
catgtacgcc gtggtgctgc tctcgtctac          30

<210> SEQ ID NO 25
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 25
ttctattttt gtacaagaca gggcttg          27

<210> SEQ ID NO 26
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 26
caagccctgt cttgtacaaa aatagaa          27

<210> SEQ ID NO 27
<211> LENGTH: 114
<212> TYPE: PRT
<213> ORGANISM: Murine R3 antibody
<220> FEATURE:
<221> NAME/KEY: MISC_FEATURE
<223> OTHER INFORMATION: Deduced amino acid sequence of VK of murine R3
      antibody

<400> SEQUENCE: 27

Asp Val Leu Met Thr Gln Ile Pro Leu Ser Leu Pro Val Ser Leu Gly
1               5                   10                  15

Asp Gly Ala Ser Ile Ser Cys Arg Ser Ser Gln Asn Ile Val His Ser
            20                  25                  30

Asn Gly Asn Thr Tyr Leu Asp Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Arg Gly Ser Gly Ser Gly Thr Asp Phe Thr Leu Lys Ile

```
                65                  70                  75                  80
Ser Arg Val Glu Ala Glu Asp Leu Gly Val Tyr Tyr Cys Phe Gln Tyr
                    85                  90                  95

Ser His Val Pro Trp Thr Phe Gly Gly Gly Thr Lys Leu Glu Ile Lys
            100                 105                 110

Arg Ala

<210> SEQ ID NO 28
<211> LENGTH: 123
<212> TYPE: PRT
<213> ORGANISM: Murine R3 antibody
<220> FEATURE:
<221> NAME/KEY: MISC_FEATURE
<223> OTHER INFORMATION: Deduced amino acid sequence of VH of murine R3
      antibody

<400> SEQUENCE: 28

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Tyr Ile Tyr Trp Val Lys Gln Arg Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Lys Ala Thr Leu Thr Val Asp Glu Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Thr Arg Gln Gly Leu Trp Phe Asp Ser Asp Gly Arg Gly Phe Asp Phe
            100                 105                 110

Gln Gly Gln Gly Thr Thr Leu Thr Val Ser Ser
        115                 120

<210> SEQ ID NO 29
<211> LENGTH: 15
<212> TYPE: PRT
<213> ORGANISM: Murine
<220> FEATURE:
<221> NAME/KEY: MISC_FEATURE
<223> OTHER INFORMATION: CDR of murine R3 antibody

<400> SEQUENCE: 29

Arg Ser Ser Gln Asn Ile Val His Ser Asn Gly Asn Thr Tyr Leu
1               5                   10                  15

<210> SEQ ID NO 30
<211> LENGTH: 7
<212> TYPE: PRT
<213> ORGANISM: Murine
<220> FEATURE:
<221> NAME/KEY: MISC_FEATURE
<223> OTHER INFORMATION: CDR of murine R3 antibody

<400> SEQUENCE: 30

Lys Val Ser Asn Arg Phe Ser
1               5

<210> SEQ ID NO 31
<211> LENGTH: 9
<212> TYPE: PRT
<213> ORGANISM: Murine
```

<220> FEATURE:
<221> NAME/KEY: MISC_FEATURE
<223> OTHER INFORMATION: CDR of murine R3 antibody

<400> SEQUENCE: 31

Phe Gln Tyr Ser His Val Pro Trp Thr
1               5

<210> SEQ ID NO 32
<211> LENGTH: 5
<212> TYPE: PRT
<213> ORGANISM: Murine
<220> FEATURE:
<221> NAME/KEY: MISC_FEATURE
<223> OTHER INFORMATION: CDR of murine R3 antibody

<400> SEQUENCE: 32

Asn Tyr Tyr Ile Tyr
1               5

<210> SEQ ID NO 33
<211> LENGTH: 17
<212> TYPE: PRT
<213> ORGANISM: Murine
<220> FEATURE:
<221> NAME/KEY: MISC_FEATURE
<223> OTHER INFORMATION: CDR of murine R3 antibody

<400> SEQUENCE: 33

Gly Ile Asn Pro Thr Ser Gly Gly Ser Asn Phe Asn Glu Lys Phe Lys
1               5                   10                  15

Thr

<210> SEQ ID NO 34
<211> LENGTH: 14
<212> TYPE: PRT
<213> ORGANISM: Murine
<220> FEATURE:
<221> NAME/KEY: MISC_FEATURE
<223> OTHER INFORMATION: CDR of murine R3 antibody

<400> SEQUENCE: 34

Gln Gly Leu Trp Phe Asp Ser Asp Gly Arg Gly Phe Asp Phe
1               5                   10

<210> SEQ ID NO 35
<211> LENGTH: 114
<212> TYPE: PRT
<213> ORGANISM: Artificial Sequence
<220> FEATURE:
<223> OTHER INFORMATION: Amino acid sequence of humanized VK of murine
      R3 antibody containing mAb CDRs

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

-continued

```
Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
               100                 105                 110

Arg Glu

<210> SEQ ID NO 36
<211> LENGTH: 123
<212> TYPE: PRT
<213> ORGANISM: Artificial Sequence
<220> FEATURE:
<223> OTHER INFORMATION: Amino acid sequence of humanized VH of murine
      R3 antibody containing mAb R3 CDRs

<400> SEQUENCE: 36

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Ile Tyr Trp Val Arg Gln Ala Pro Gly Gln Gly Leu Glu Trp Ile
            35                  40                  45

Gly Gly Ile Asn Pro Thr Ser Gly Gly Ser Asn Phe Asn Glu Lys Phe
        50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
               100                 105                 110

Trp Gly Gln Gly Ser Thr Val Thr Val Ser Ser
            115                 120
```